(12) United States Patent
Eite

(10) Patent No.: US 12,028,943 B2
(45) Date of Patent: Jul. 2, 2024

(54) LAMINATED SUBSTRATE

(71) Applicant: Diamond Coatings Ltd., Halesowen (GB)

(72) Inventor: Jason Eite, Halesowen (GB)

(73) Assignee: Diamond Coatings Ltd. (GB)

( * ) Notice: Subject to any disclaimer, the term of this patent is extended or adjusted under 35 U.S.C. 154(b) by 853 days.

(21) Appl. No.: 16/981,484

(22) PCT Filed: Mar. 19, 2019

(86) PCT No.: PCT/GB2019/050757
§ 371 (c)(1),
(2) Date: Sep. 16, 2020

(87) PCT Pub. No.: WO2019/180416
PCT Pub. Date: Sep. 26, 2019

(65) Prior Publication Data
US 2021/0029784 A1    Jan. 28, 2021

(30) Foreign Application Priority Data
Mar. 19, 2018  (GB) ..................... 1804340

(51) Int. Cl.
| H05B 3/84 | (2006.01) |
| A42B 3/24 | (2006.01) |
| A61F 9/02 | (2006.01) |
| B32B 3/08 | (2006.01) |
| B32B 7/12 | (2006.01) |

(Continued)

(52) U.S. Cl.
CPC ............... *H05B 3/84* (2013.01); *A42B 3/245* (2013.01); *A61F 9/029* (2013.01); *B32B 3/08* (2013.01); *B32B 7/12* (2013.01); *B32B 15/09* (2013.01); *H05B 3/141* (2013.01); *H05B 3/36* (2013.01); *B32B 2255/10* (2013.01); *B32B 2255/20* (2013.01); *B32B 2307/412* (2013.01); *B32B 2551/00* (2013.01); *H05B 2203/011* (2013.01);

(Continued)

(58) Field of Classification Search
CPC . H05B 3/84; H05B 3/141; H05B 3/36; H05B 2203/011; H05B 2203/013; H05B 2203/016
See application file for complete search history.

(56) References Cited

U.S. PATENT DOCUMENTS

| 4,828,346 A | 5/1989 | Jacobson et al. |
| 5,351,339 A | 10/1994 | Reuber et al. |

(Continued)

FOREIGN PATENT DOCUMENTS

| CN | 107114848 A | 9/2017 |
| EP | 2103978 A1 | 9/2009 |

(Continued)

OTHER PUBLICATIONS

The International Search Report and Written Opinion issued on May 31, 2019 for International Patent Application No. PCT/GB2019/050757; pp. 1-12.

(Continued)

*Primary Examiner* — Brian W Jennison
(74) *Attorney, Agent, or Firm* — Bell & Manning, LLC

(57) ABSTRACT

The present invention provides a laminated substrate for use as an anti-fogging insert for an eye shield, more particularly for use as a heated anti-fogging insert for a visor or goggles.

16 Claims, 3 Drawing Sheets

(51) Int. Cl.
  *B32B 15/09* (2006.01)
  *H05B 3/14* (2006.01)
  *H05B 3/36* (2006.01)
(52) U.S. Cl.
  CPC .. *H05B 2203/013* (2013.01); *H05B 2203/016* (2013.01)

(56) References Cited

U.S. PATENT DOCUMENTS

| | | | |
|---|---|---|---|
| 5,459,533 | A | 10/1995 | McCooeye et al. |
| 5,694,650 | A | 12/1997 | Hong |
| 6,417,491 | B1 | 7/2002 | Taniuchi |
| 2008/0290081 | A1 | 11/2008 | Biddell |
| 2013/0091623 | A1 | 4/2013 | McCulloch et al. |
| 2013/0212765 | A1 | 8/2013 | Cornelius |
| 2014/0317836 | A1 | 10/2014 | McCulloch et al. |
| 2014/0319116 | A1 | 10/2014 | Fischer et al. |
| 2014/0362434 | A1 | 12/2014 | Schmitz et al. |
| 2016/0044747 | A1 | 2/2016 | Prins et al. |
| 2017/0143546 | A1 | 5/2017 | O'Malley |
| 2018/0052319 | A1* | 2/2018 | McCabe ................ A61F 9/029 |

FOREIGN PATENT DOCUMENTS

| | | |
|---|---|---|
| EP | 3290965 A1 | 3/2018 |
| WO | WO 2013/104439 A1 | 7/2013 |
| WO | WO 2016/123119 A1 | 8/2016 |

OTHER PUBLICATIONS

UKIPO Search Report issued on Sep. 19, 2018 for application No. GB1804340.6; pp. 1-4.

* cited by examiner

LAMINATED SUBSTRATE

This application is a National Stage of International Application No. PCT/GB2019/050757, filed Mar. 19, 2019, which claims the benefit of GB Patent Application No. GB1804340.6, filed Mar. 19, 2018, the contents of which are herein incorporated by reference.

The present invention relates to a laminated substrate for use as an anti-fogging insert for an eye shield, more particularly for use as a heated anti-fogging insert for a visor or goggles.

BACKGROUND

Protective helmets, such as for motorcycle or snowmobile riding, typically have transparent visors, or eye shields, and protective goggles for use when skiing, snowboarding, diving etc, are known to fog in certain weather conditions such as rain or cold weather, reducing visibility for the wearer.

Pinlock Fog Free Systems® address the problem of fogging by the provision of a visor insert which comprises a moisture absorbing layer and a silicon seal. However, excessive moisture can cause this system to fail, resulting in visible drops or lines of water on the visor and a corresponding loss of visibility.

US2008/0290081A1 discusses the use of a heater element formed of an etched metal form as an anti-fogging device, while U.S. Pat. No. 5,351,339 discusses the use of an electroconductive film.

These known devices all have a high degree of reflection on the inside of the visor or goggles which can interfere with the user's field of vision. In particular, indium tin oxide (ITO), a commonly used transparent conductive oxide (TCO), has a refractive index of 2, resulting in high reflection for the user of such products.

SUMMARY OF THE INVENTION

The invention provides a laminated anti-fogging insert for an eye shield, comprising:
  a) a substrate which is a flexible transparent film;
  b) a first and second metal strip, which metal strips are applied to respective non-adjacent edges of the substrate;
  c) at least two electrical connectors independently positioned at one end of each of the first and second conductive metal strips;
  d) a conductive layer which partially overlaps the metal strips; and
  e) an index-matching layer.

The invention further provides an eye shield comprising a lens and a laminated anti-fogging insert, which laminated anti-fogging device comprises:
  a) a substrate which is a flexible transparent film;
  b) a first and second metal strip, which metal strips are applied to respective non-adjacent edges of the substrate;
  c) at least two electrical connectors independently positioned at one end of each of the first and second conductive metal strips;
  d) a conductive layer which partially overlaps the metal strips;
  e) an index-matching layer; and
  f) a first attachment means for attaching the laminated anti-fogging insert to the lens, thereby defining a sealed air gap between the lens and the insert.

The invention further provides a process for preparing a laminated anti-fogging insert or eye shield, comprising:
  a) providing a substrate which is a flexible transparent film;
  b) optionally masking parts of the first layer;
  c) applying a first and second metal strip;
  d) applying a conductive layer;
  e) applying an index-matching layer; and
  f) optionally applying a first attachment means to the periphery of the laminated anti-fogging insert.

DETAILED DESCRIPTION

Figure 1:
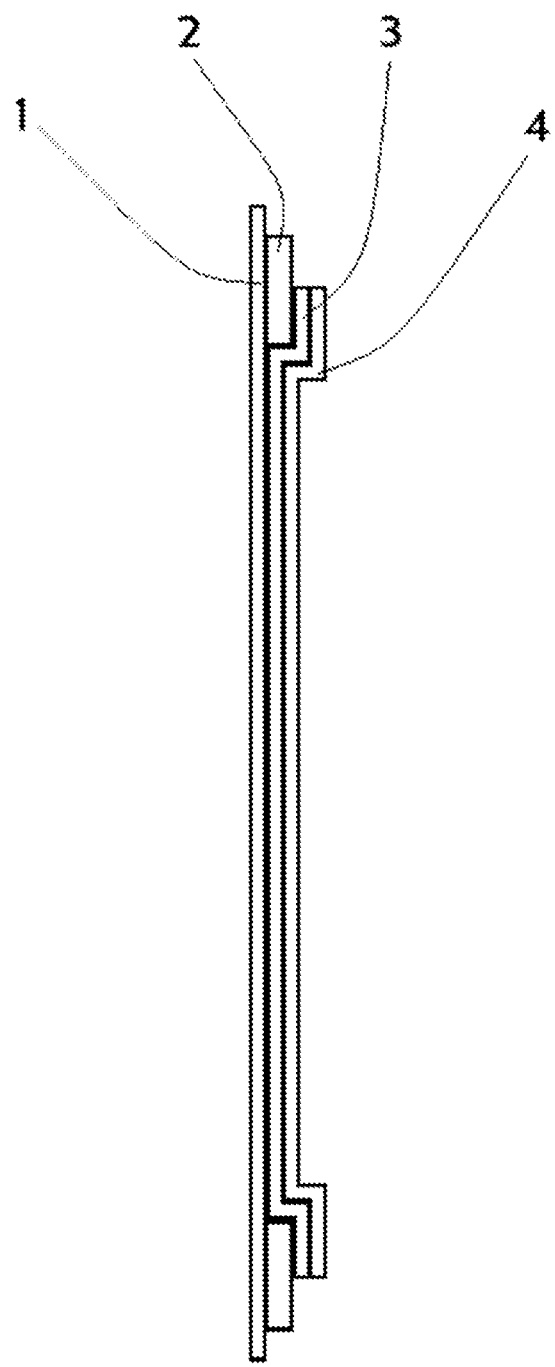
FIG. 1 illustrates in cross-section the laminated anti-fogging insert of the invention.

FIG. 1 illustrates a laminated anti-fogging insert for an eye shield comprising a substrate which is a flexible transparent film (1), first and second metal strips (2), a conductive layer (3) which partially overlaps the metal strips, and an index matching layer (4).

Figure 2:
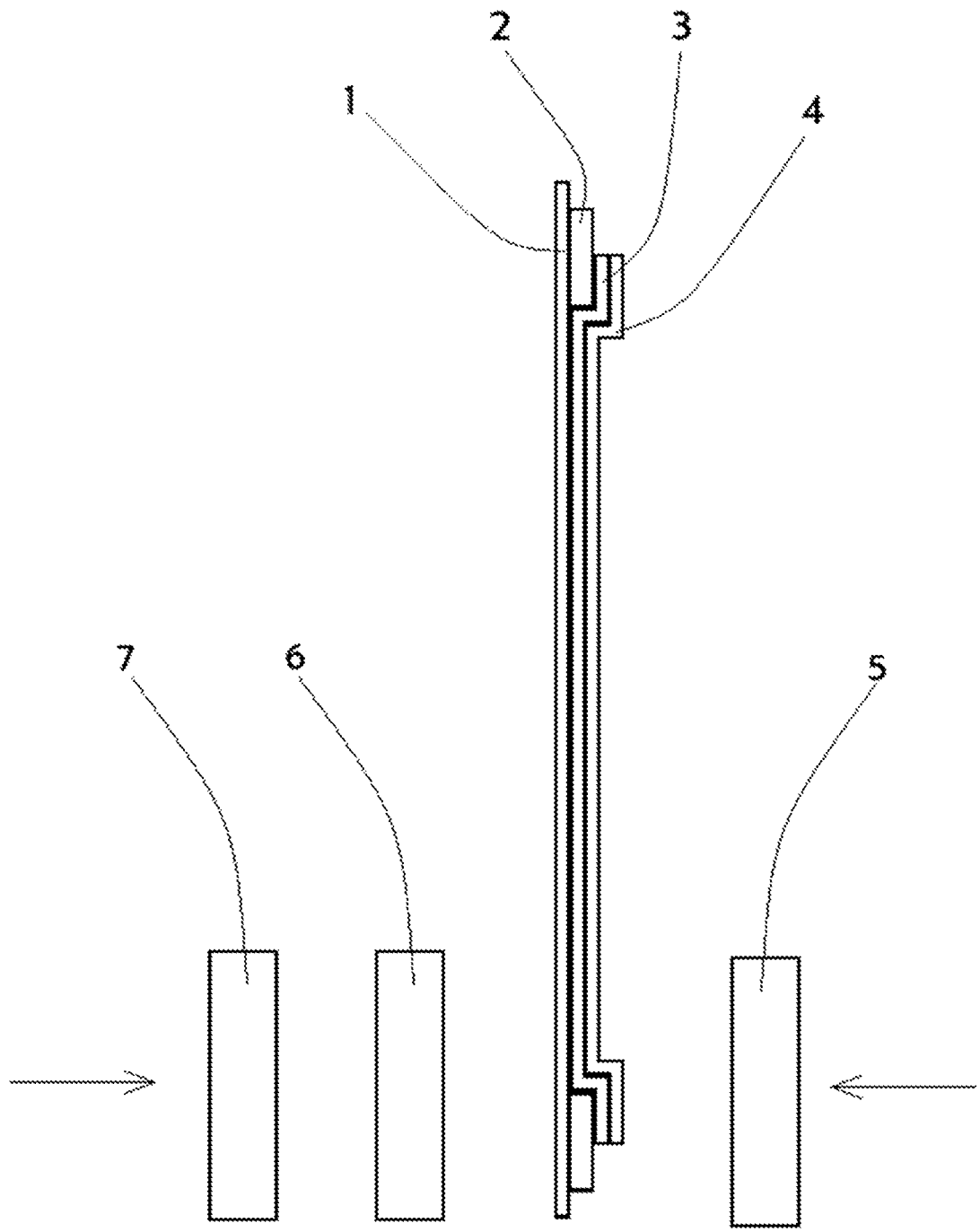
FIG. 2 illustrates in cross-section means for attaching the laminated anti-fogging insert of the invention to an eye shield.

FIG. 2 illustrates a laminated anti-fogging insert for an eye shield which further comprises a first attachment means (5) for attaching the laminated anti-fogging insert to the lens, thereby defining a sealed air gap between the lens and the insert; and formed supports (7) which are attached to the index matching layer (4) by a second attachment means (6) and which hold in place electrical connectors (8a, 8b—not shown) connected to the metal strips (2).

Figure 3:
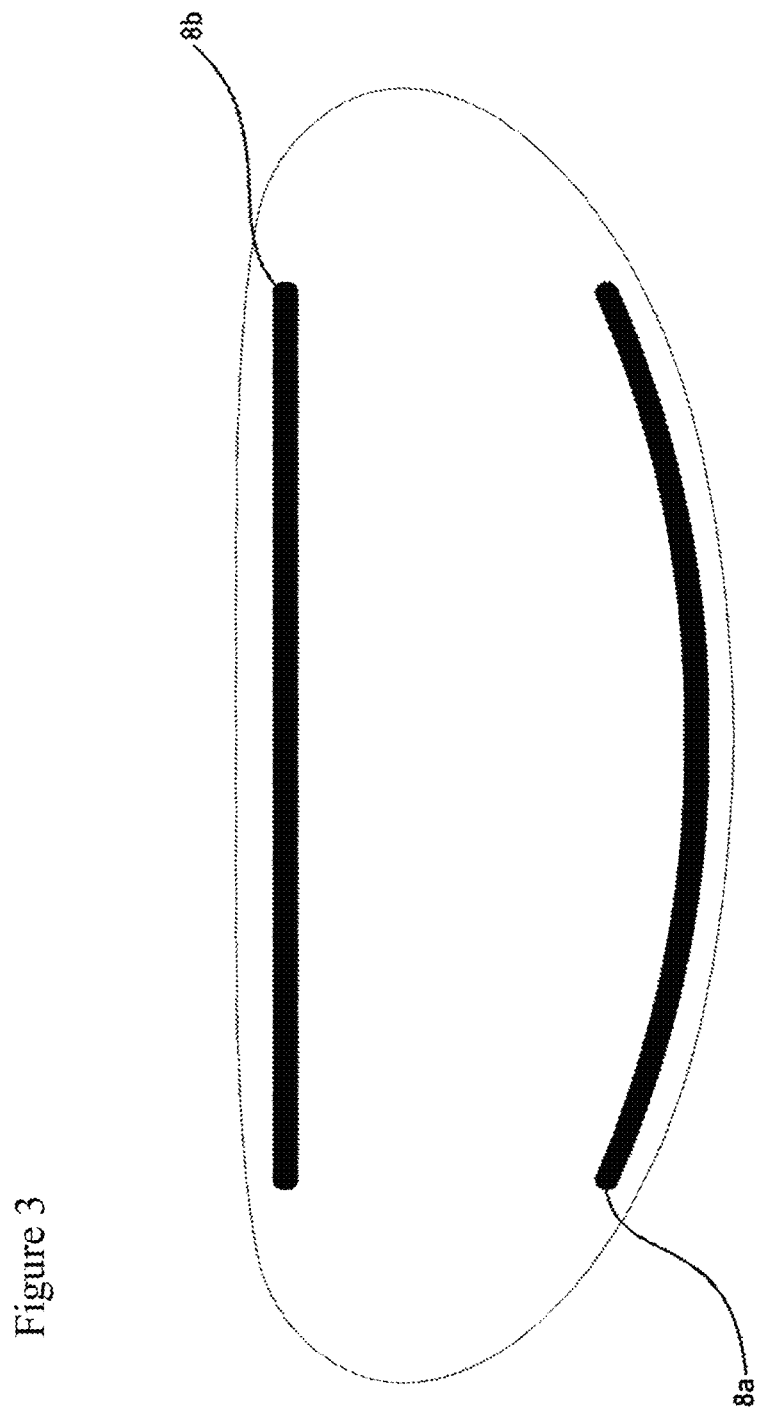
FIG. 3 illustrates in plan-view a preferred positioning of the electrical connectors at opposing ends of the first and second metal strips.

FIG. 3 illustrates a laminated anti-fogging insert for an eye shield wherein the electrical connectors (8a and 8b) are positioned at opposing ends of the first and second conductive metal strips.

Accordingly, the invention is described by the following embodiments.

In embodiment 1, the invention provides a laminated anti-fogging insert for an eye shield, comprising:
  a) a substrate which is a flexible transparent film;
  b) a first and second metal strip, which metal strips are applied to respective non-adjacent edges of the substrate;
  c) at least two electrical connectors independently positioned at one end of each of the first and second conductive metal strips;
  d) a conductive layer which partially overlaps the metal strips; and
  e) an index-matching layer.

In embodiment 2, the invention provides a laminated anti-fogging insert according to embodiment 1, wherein the substrate is formed of a suitable transparent plastic, such as Polyethylene Terephthalate (PET), Polycarbonate (PC), Acrylic (PMMA), Cyclic Olefin Copolymer (COC), Cyclic Olefin Polymer (COP), Thermoplastic polyurethane (TPU), Ethylene vinyl acetate (EVA), Polyvinylidene fluoride or polyvinylidene difluoride (PVDF), Ethylene tetrafluoroethylene (ETFE) or polyethylene-naphthalate (PEN) film.

In embodiment 3, the invention provides a laminated anti-fogging insert according to embodiment 1 or 2, wherein the substrate is formed of polyethylene terephthalate (PET), preferably temperature stabilised polyethylene terephthalate.

In embodiment 4, the invention provides a laminated anti-fogging insert according to any previous embodiment, wherein the substrate has a thickness of from 125 to 200 µm; preferably from 150 to 200 µm; preferably from 170 to 180 µm; more preferably around 175 µm.

In embodiment 5, the invention provides a laminated anti-fogging insert according to any previous embodiment, wherein the first and second metal strips are formed of a metal selected from the group consisting of silver, copper, nickel, gold, carbon, and alloys or mixtures thereof.

In embodiment 6, the invention provides a laminated anti-fogging insert according to any previous embodiment, wherein the first metal strip is one continuous strip.

In embodiment 7, the invention provides a laminated anti-fogging insert according to any previous embodiment, wherein the first metal strip is divided into two or more sections.

In embodiment 8, the invention provides a laminated anti-fogging insert according to any previous embodiment, wherein the second metal strip is one continuous strip.

In embodiment 9, the invention provides a laminated anti-fogging insert according to any previous embodiment, wherein the second metal strip is divided into two or more sections.

In embodiment 10, the invention provides a laminated anti-fogging insert according to any previous embodiment, wherein the at least two electrical connectors are positioned at opposing ends of the first and second metal strips.

In embodiment 11, the invention provides a laminated anti-fogging insert according to any previous embodiment, wherein the conductive layer comprises a transparent conducting oxide, a transparent conducting polymer, or graphene, silver nano-wires or printed micro-lines.

In embodiment 12, the invention provides a laminated anti-fogging insert according to any previous embodiment, wherein the conductive layer comprises a transparent conducting oxide (TCO). The TCO may be an n-type or a p-type TCO and may be a simple, binary or ternary oxide of a metal from the $2^{nd}$, $3^{rd}$, $4^{th}$, $5^{th}$, $6^{th}$, $7^{th}$ or period or the periodic table, or a lanthanide metal.

In embodiment 13, the invention provides a laminated anti-fogging insert according to any previous embodiment, wherein the conductive layer comprises a transparent conducting oxide selected from an oxide of a metal selected from Al, Ga, In, Sn, Tl, Pb, Bi, Nh, Fl, Mc and Lv or combinations thereof. Preferably, the TCO is selected from the group consisting of tin oxide ($SnO_2$), indium oxide ($In_2O_3$), zinc oxide (ZnO), cadmium oxide (CdO), indium tin oxide (ITO), fluorine doped ZnO, aluminium doped ZnO (ZnO:Al), $Cd_2SnO_4$, $Zn_2SnO_4$, $MgIn_2O_4$, $CdSb_2O_6$:Y, $ZnSnO_3$, $GaInO_3$, $Zn_2In_2O_5$, $In_4Sn_3O_{12}$, ZnO:Ga;

In embodiment 14, the invention provides a laminated anti-fogging insert according to any previous embodiment, wherein the conductive layer comprises indium tin oxide (ITO).

The conductive layer of the present invention has a sheet resistance which is chosen to achieve an offset of ½ the wavelength of light (lambda), alternatively 1.5 or 2.5 lambda. In practise, the sheet resistance will vary depending on the thickness of the index matching layer, however, in order to achieve an offset of ½ lambda, a sheet resistance of about 50 ohms is suitable, which may be varied depending on the thickness of the index matching layer.

In embodiment 15, the invention provides a laminated anti-fogging insert according to any previous embodiment, wherein the conductive layer has a sheet resistance of from 25 Ohms/square to 75 Ohms/square; preferably from 40 to 60 Ohms/square; more preferably about 50 Ohms/square.

In embodiment 16, the invention provides a laminated anti-fogging insert according to any previous embodiment, wherein the conductive layer has a thickness of from 80 to 120 nm; preferably from 90 to 110 nm; more preferably about 100 nm.

In embodiment 17, the invention provides a laminated anti-fogging insert according to any previous embodiment, wherein the conductive layer is a continuous film.

In embodiment 18, the invention provides a laminated anti-fogging insert according to any previous embodiment, wherein the conductive layer is not a continuous film.

In embodiment 19, the invention provides a laminated anti-fogging insert according to any previous embodiment, wherein the index-matching layer comprises a low refractive index material such as silicon oxide, magnesium fluoride and fluorinated polymers; or a high refractive index material, such as titanium oxide, vanadium oxide, zirconium oxide, niobium oxide, hafnium oxide, tantalum oxide; or a mixture thereof.

It will be appreciated that the index-matching layer may comprise a single layer of one or more materials as described in embodiment 19, or alternatively, the index matching layer may comprise a number of sub-layers of the same or different materials which are matched so as to produce the desired offset in the wavelength of light.

In embodiment 20, the invention provides a laminated anti-fogging insert according to any previous embodiment, wherein the index-matching layer comprises at least one low refractive index material, preferably silicon oxide, and at least one high refractive index material.

In embodiment 21, the invention provides a laminated anti-fogging insert according to any previous embodiment, wherein the index-matching layer has a thickness of from 80 to 90 nm; preferably around 85 nm.

In embodiment 22, the invention provides a laminated anti-fogging insert according to any previous embodiment, wherein the index-matching layer has a thickness of about ¼ wavelength of light (¼ lambda).

In embodiment 23, the invention provides a laminated anti-fogging insert according to any previous embodiment, wherein the insert comprises a first and second index-matching layer so that the conductive layer is sandwiched between two index matching layers. The laminated anti-fogging insert according to this embodiment comprises:
 a) a substrate which is a flexible transparent film;
 b) a first and second metal strip, which metal strips are applied to respective non-adjacent edges of the substrate;
 c) at least two electrical connectors independently positioned at one end of each of the first and second conductive metal strips;
 d) a first index-matching layer;
 e) a conductive layer which partially overlaps the metal strips; and
 f) a second index matching layer.

In embodiment 24, the invention provides a laminated anti-fogging insert according to embodiment 23, wherein each of the first and second index-matching layers independently comprise a low refractive index material such as silicon oxide, magnesium fluoride and fluorinated polymers; or a high refractive index material, such as titanium oxide, vanadium oxide, zirconium oxide, niobium oxide, hafnium oxide, tantalum oxide; or a mixture thereof. Preferably, each index-matching layer independently comprises at least one low refractive index material and at least one high refractive index material. More preferably at least one index-matching layer comprises silicon oxide and optionally a high refractive index material.

In embodiment 25, the invention provides a laminated anti-fogging insert according to embodiment 23 or 24, wherein the first index-matching layer comprises a low refractive index material and the second index-matching layer comprises a high refractive index material; or the first index-matching layer comprises a high refractive index material and the second index-matching layer comprises a low refractive index material.

In embodiment 26, the invention provides a laminated anti-fogging insert according to any previous embodiment, wherein the insert further comprises formed supports which are attached to the index-matching layer by a second attachment means and which hold in place the electrical conductors. The formed supports are suitably formed of rubber. The formed supports may be attached to the conductive layer by any suitable attachment means, preferably by adhesive gaskets.

In embodiment 27, the invention provides a laminated anti-fogging insert according to any previous embodiment, wherein each electrical connector is independently attached to the first or second metal strips, and at the opposite end to a power source.

In embodiment 28, the invention provides a laminated anti-fogging insert according to any previous embodiment, wherein the power source is a battery; or a power source mounted on or in a vehicle.

In embodiment 29, the invention provides an eye shield comprising a lens; a laminated anti-fogging insert according to any previous embodiment; and a first attachment means for attaching the laminated anti-fogging insert to the lens, thereby defining a sealed air gap between the lens and the insert.

In embodiment 30, the invention provides an eye shield according to embodiment 29, wherein the first attachment means is selected from a silicon seal, a gasket, and an adhesive strip; preferably the first attachment means comprises an adhesive foam gasket.

In embodiment 31, the invention provides an eye shield according to embodiment 29 or 30, wherein the eye shield is selected from a protective helmet visor and protective goggles.

In embodiment 32, the invention provides an eye shield according to any one of embodiments 29 to 31, wherein the eye shield is a motorcycle helmet visor, snowmobile helmet visor, ski or snowboard helmet visor; and ski or snowboard goggles.

In embodiment 33, the invention provides an eye shield according to any one of embodiments 29 to 32, wherein the eye shield is selected from ski and snowboard goggles.

In embodiment 34, the invention provides a process for preparing a laminated anti-fogging insert or eye shield according to any one of embodiments 1 to 28, comprising:
  g) providing a substrate which is a flexible transparent film;
  h) optionally masking parts of the first layer;
  i) applying a first and second metal strip;
  a) applying a conductive layer;
  b) applying an index-matching layer; and
  c) optionally applying a first attachment means to the periphery of the laminated anti-fogging insert.

In embodiment 35, the invention provides a process according to embodiment 34, wherein the conductive layer of step d) and the index-matching layer of step e) are each independently applied using any suitable deposition means, preferably physical vapour deposition or chemical vapour deposition.

In embodiment 36, the invention provides a kit comprising:
  a) a laminated anti-fogging insert according to any one of embodiments 1 to 28;
  b) a first attachment means;
  c) one or more electrical connectors; and
  d) optionally one or more batteries.

In embodiment 37, the invention provides a laminated anti-fogging insert comprising
  a) a substrate comprising polyethylene terephthalate (PET);
  b) a first and second silver strip, which silver strips are applied to respective non-adjacent edges of the substrate;
  c) at least two electrical connectors independently positioned at one end of each of the first and second silver strips;
  d) a conductive layer which partially overlaps the metal strips, wherein the conductive layer comprises a transparent conducting oxide, and preferably comprises indium tin oxide; and
  e) an index matching layer comprising silicon oxide and optionally a high refractive index material.

In embodiment 38, the invention provides an eye shield comprising a lens; a laminated anti-fogging insert according to embodiment 37; and a first attachment means for attaching the laminated anti-fogging insert to the lens, thereby defining a sealed air gap between the lens and the insert, wherein the first attachment means comprises an adhesive foam gasket.

In embodiment 39, the invention provides a kit comprising:
  a) a laminated anti-fogging insert according to embodiment 37;
  b) a first attachment means which is an adhesive foam gasket;
  c) one or more electrical connectors; and
  d) optionally one or more batteries.

Definitions

The term 'index-matching' as used herein refers to a layer or a number of sub-layers of a material or mixture of materials which has an index of refraction that is 'matched' to the thickness of the conductive layer so as to achieve a reduction in reflection. The skilled person will appreciate that the thickness of the index matching layer (eg silicon oxide) can vary depending on the thickness and sheet conductivity of the conductive layer (eg ITO). The index matching layer preferably has a thickness sufficient to achieve an offset of ½ lambda (or 1.5 or 2.5 lambda). The index-matching layer may comprise a single material or the layer may comprise both a high refractive index and a low refractive index material. The index-matching layer may comprise a single layer or may comprise a number of sub-layers which may each comprise one or more materials chosen to achieve the desired offset of an offset of ½ lambda (or 1.5 or 2.5 lambda). The use of two different materials in order to achieve the desired offset is known as a Herpin equivalent pair. The index-matching layer of the present invention may comprise a Herpin equivalent pair of materials.

Alternatively, the laminated anti-fogging insert of the invention may comprise two index-matching layers, wherein one layer comprises a low refractive index material and one layer comprises a high refractive index material.

A single layer film, such as an ITO, in air will cause additional reflection if it's refractive index is higher than the refractive index of the substrate. ITO has a refractive index of around 2, compared with a refractive index for most polymers of around 1.5. When applied to a laminated insert, this may cause a reflection of up to 20% whereas the substrate polymer surface has a reflection of 4%.

The single ITO film has 2 interfaces and there is reflection at each, which is roughly proportional to the square of the refractive index difference at the interface. Therefore, there is much greater reflection at the ITO/air interface (refractive index difference=2−1=1, $1^2$=1), than at the ITO/substrate interface (refractive index difference=2−1.5=0.5, $0.5^2$=0.25).

The index-matching layer of the present invention adds a layer to one side of the conductive layer.

For example, a $SiO_2$ index-matching layer applied to the air side of an ITO film (substrate/ITO/$SiO_2$/air) may reduce the reflection from 20% to 2%. Where an index-matching (IM) layer is applied to both sides of the ITO film (substrate/IM/ITO/$SiO_2$/air), the reflection may be decreased to around 0.3%.

It will be appreciated that the metal strips (also known as busbars) may be parallel; or alternatively, one or both busbars may be curved so that the ends of each respective metal strip are closer together than the mid-part of each strip. It has been found that when one or both metal strips (busbars) are curved, heating of the conductive film is faster and there is more uniform clearance of fog.

Each metal strip may be one continuous strip or may be divided to comprise two or more strip elements, separated by small breaks. For example, a strip may comprise two strip elements shaped to fit either side of the nose region of the insert.

The term 'at least two' as used herein, refers to two or more, suitably 2 or 3 or 4 or 5 or 6 or 7 or 8.

The term 'electrical connector' as used herein, refers collectively to any suitable wires or cables and to means for connecting the electrical wires or cables to the first and second metal strips, thereby creating an electrical circuit. The electrical connector suitably comprises a flexible wire or cable which may be straight or coiled.

The term 'transparent conducting oxide (TCO) as used herein, refers to an electrical conductive material with a comparably low absorption of light. TCOs comprise a metal oxide, which may be doped with other metals or with non-metals. Suitable TCOs for use in the invention are those disclosed by Stadler (*Materials*, 2012, 5, 661-683) and Ginley and Bright (*MRS Bulletin*, August 2000, 15-18). Both n-type and p-type TCOs are known, and a combination of both n- and p-type may be used. Examples of p-type TCOs include: Delafossites, which are ternary material combinations of copper (Cu), one or more further metals (A) and oxygen (O)—$Cu_xA_yO_z$, wherein copper may be replaced with silver, palladium, or platinum, and the dopant, A, may be iron, cobalt, chrome, strontium, barium, aluminium, gallium, indium, scandium, yttrium and lanthanum; and Mayenites, which are ternary material combinations of magnesium (Mg), one or more further metals (eg zirconium (Zn) or aluminium (Al)), and oxygen (O). Examples of n-type TCOs include tin oxide ($SnO_2$), indium oxide ($In_2O_3$), zinc oxide (ZnO), cadmium oxide (CdO), indium tin oxide (ITO), fluorine doped ZnO, aluminium doped ZnO (ZnO:Al), $Cd_2SnO_4$, $Zn_2SnO_4$, $MgIn_2O_4$, $CdSb_2O_6$:Y, $ZnSnO_3$, $GaInO_3$, $Zn_2In_2O_5$, $In_4Sn_3O_{12}$, ZnO:Ga. Preferably the TCO for use in the invention is selected from the group consisting of NiO, ZnO, $Cr_2O_3$, $CuCrO_2$ (Delafossite), $Mg_{1-x}Zn_xO$:In, $Mg_{1-x}Zn_xO$:Al, $Mg_{12}Al_{14}O_{33}$ (Mayenite), tin oxide ($SnO_2$), indium oxide ($In_2O_3$), zinc oxide (ZnO), cadmium oxide (CdO), indium tin oxide (ITO), fluorine doped ZnO, aluminium doped ZnO (ZnO:Al), $Cd_2SnO_4$, $Zn_2SnO_4$, $MgIn_2O_4$, $CdSb_2O_6$:Y, $ZnSnO_3$, $GaInO_3$, $Zn_2In_2O_5$, $In_4Sn_3O_{12}$, and ZnO:Ga.

More preferably the TCO is an oxide of a metal selected from Zn, Al, Ga, In, Sn, Tl, Pb, Bi, Nh, Fl, Mc, Lv, and combinations thereof. Most preferably the TCO is indium tin oxide (ITO).

The term 'deposition means' as used herein refers to a process for depositing thin films various means and includes both chemical and physical vapour deposition. In chemical vapour deposition, the substrate is exposed to one or more volatile source material which react and/or decompose on the substrate surface to produce the thin film. Physical vapour deposition is typically either: thermal vapour deposition where the source material is heated to produce a vapour which is condensed as a thin film on the substrate; or sputtering, comprising eroding material from a source onto a substrate.

The laminated anti-fogging insert of the present invention, when attached to a visor or to goggles, operates by applying an electrical current to the conductive layer so that the conductive layer is heated to a suitable temperature, such as around 30° C. The electrical current may be provided by any suitable power source such as a battery. Alternatively, the electrical current may be provided by a power source mounted on a vehicle, such as a motorcycle.

The laminated anti-fogging insert of the invention may be prepared as described in the following examples.

EXAMPLE 1

A laminated anti-fogging insert according to the invention and as illustrated in FIG. 1 was prepared by the following process.

A substrate (1) was prepared by cutting sheets of temperature stabilised polyethylene terephthalate (PET) film with a thickness of 175 μm to the desired shape. Silver metal strips (busbars) (2) were applied to opposite edges of the substrate using screen printing, and thermally cured.

Masking tape was applied to a portion of each busbar, leaving a portion of each busbar and the area in between the busbars unmasked.

A layer of indium tin oxide (ITO) (3) was applied to the non-masked area to a thickness of 100 nm using physical vapour deposition in a vacuum chamber. The ITO layer was applied as a continuous film covering the area between the busbars and a portion of each busbar.

A layer of silica (4) was then applied to a thickness of 84 nm using physical vapour deposition in a vacuum chamber and the masking tape was removed.

Electrical connectors (8a, 8b) were provided at opposing ends of the first and second silver metal strips (busbars) (2), as illustrated in FIG. 3. The arrangement of electrical connectors (8a, 8b) at opposing ends of the metal strips (2) was found to provide more uniform heating across the conductive film area.

EXAMPLE 2

A laminated anti-fogging insert as illustrated in FIG. 2 was prepared as described in Example 1. Rubber mouldings as formed supports (7) with cable strain reliefs were attached to the aminated insert using adhesive gaskets (6). The formed supports (7) serve to hold the electrical connectors (8a, 8b—FIG. 3)) in place. An adhesive foam gasket (5) was provided for attaching the laminated anti-fogging insert to an eye shield.

The invention claimed is:

1. An anti-fogging insert for an eye shield, comprising:
   a) a substrate which is a flexible transparent film;
   b) a first and second metal strip, which metal strips are applied to respective non-adjacent edges of the substrate;
   c) at least two electrical connectors independently positioned at one end of each of the first and second conductive metal strips;
   d) a conductive layer which partially overlaps the metal strips; and
   e) an index-matching layer;
   wherein the index-matching layer is in direct contact with the conductive layer.

2. An anti-fogging insert according to claim 1, wherein the conductive layer comprises a transparent conducting oxide (TCO).

3. An anti-fogging insert according to claim 1, wherein the conductive layer has a thickness of from 80 to 120 nm.

4. An anti-fogging insert according to claim 1, wherein the index-matching layer comprises a low refractive index material selected from the group consisting of silicon oxide, magnesium fluoride, fluorinated polymers, and combinations thereof.

5. An anti-fogging insert according to claim 1, wherein the index-matching layer has a thickness of about ¼ wavelength of light (¼ lambda).

6. An anti-fogging insert according to claim 1, wherein the insert comprises a first and second index-matching layer so that the conductive layer is sandwiched between two index matching layers.

7. An anti-fogging insert according to claim 6, wherein the first index-matching layer comprises a low refractive index material and the second index-matching layer comprises a high refractive index material; or the first index-matching layer comprises a high refractive index material and the second index-matching layer comprises a low refractive index material.

8. An anti-fogging insert according to claim 1, wherein the substrate is formed of a flexible transparent plastic selected from Polyethylene Terephthalate (PET), Polycarbonate (PC), Acrylic (PMMA), Cyclic Olefin Copolymer (COC), Cyclic Olefin Polymer (COP), Thermoplastic polyurethane (TPU), Ethylene vinyl acetate (EVA), Polyvinylidene fluoride or polyvinylidene difluoride (PVDF), Ethylene tetrafluoroethylene (ETFE) and Polyethylene-naphthalate (PEN) film.

9. An eye shield comprising:
   a lens;
   an anti-fogging insert comprising:
      a) a substrate which is a flexible transparent film;
      b) a first and second metal strip, which metal strips are applied to respective non-adjacent edges of the substrate;
      c) at least two electrical connectors independently positioned at one end of each of the first and second conductive metal strips;
      d) a conductive layer which partially overlaps the metal strips; and
      e) an index-matching layer, wherein the index-matching layer is in direct contact with the conductive layer;
   and a first attachment means for attaching the anti-fogging insert to the lens, thereby defining a sealed air gap between the lens and the insert.

10. An eye shield according to claim 9, wherein the eye shield is selected from a protective helmet visor and protective goggles.

11. A kit comprising:
    an anti-fogging insert comprising:
       a) a substrate which is a flexible transparent film;
       b) a first and second metal strip, which metal strips are applied to respective non-adjacent edges of the substrate;
       c) at least two electrical connectors independently positioned at one end of each of the first and second conductive metal strips;
       d) a conductive layer which partially overlaps the metal strips; and
       e) an index-matching layer, wherein the index-matching layer is in direct contact with the conductive layer;
    a first attachment means; and
    optionally one or more batteries.

12. An anti-fogging insert according to claim 1, wherein the anti-fogging insert is laminated.

13. An anti-fogging insert according to claim 1, wherein the substrate is proximal to a wearer when the eye shield is worn.

14. An anti-fogging insert according to claim 1, wherein the index matching layer is distal to a wearer when the eye shield is worn.

15. An eye shield according to claim 9, wherein the anti-fogging insert is laminated.

16. A kit according to claim 11, wherein the anti-fogging insert is laminated.

* * * * *